US008186777B2

(12) United States Patent
Broemsen et al.

(10) Patent No.: US 8,186,777 B2
(45) Date of Patent: May 29, 2012

(54) SAFETY WORKBENCH HAVING EASY-TO-CLEAN FRONT PANE

(75) Inventors: Olaf Broemsen, Moerfelden (DE); Christoph Noll, Gruendau (DE); Edmund Frickel, Gruendau (DE)

(73) Assignee: Thermo Electron LED GmbH, Langenselbold (DE)

( * ) Notice: Subject to any disclaimer, the term of this patent is extended or adjusted under 35 U.S.C. 154(b) by 694 days.

(21) Appl. No.: 11/959,365

(22) Filed: Dec. 18, 2007

(65) Prior Publication Data

US 2008/0163799 A1 Jul. 10, 2008

(30) Foreign Application Priority Data

Dec. 20, 2006 (DE) ........................ 10 2006 060 407

(51) Int. Cl.
*A61B 19/02* (2006.01)

(52) U.S. Cl. ........................................................ 312/209

(58) Field of Classification Search ............... 312/139.2, 312/209, 138.1, 137, 140.4, 349, 286, 292; 144/285, 286.1, 286.5, 287; 600/20, 21; 49/50, 360, 404
See application file for complete search history.

(56) References Cited

U.S. PATENT DOCUMENTS

| | | | | |
|---|---|---|---|---|
| 94,016 | A * | 8/1869 | Mayo | 312/139.2 |
| 364,448 | A * | 6/1887 | Steinfeld | 312/118 |
| 1,186,642 | A * | 6/1916 | Alamy | 312/114 |
| 1,749,177 | A * | 3/1930 | Baxter et al. | 312/139.2 |
| 2,037,413 | A * | 4/1936 | Gloekler | 312/138.1 |
| 4,054,338 | A * | 10/1977 | Martin | 312/249.5 |
| 5,069,512 | A * | 12/1991 | Sykes | 312/139.2 |
| 5,316,733 | A * | 5/1994 | Rune et al. | 422/565 |
| 6,058,523 | A * | 5/2000 | Sleboda | 4/619 |
| 6,241,328 | B1 * | 6/2001 | Ziff | 312/1 |
| 6,771,177 | B2 * | 8/2004 | Alderman | 340/585 |
| 7,006,876 | B2 | 2/2006 | Ross | |
| 2003/0193272 | A1 * | 10/2003 | Bryan | 312/1 |
| 2003/0197450 | A1 * | 10/2003 | Ross | 312/236 |
| 2003/0222087 | A1 | 12/2003 | Frickel | |
| 2004/0164660 | A1 * | 8/2004 | Delph | 312/334.25 |
| 2005/0044799 | A1 | 3/2005 | Kinross et al. | |

FOREIGN PATENT DOCUMENTS

| | | | |
|---|---|---|---|
| DE | 3617821 | A1 | 12/1986 |
| DE | 44 41 784 | A1 | 5/1996 |
| DE | 4441784 | A1 | 5/1996 |

(Continued)

OTHER PUBLICATIONS

European Search Report dated Mar. 20, 2008, 3 pages.

*Primary Examiner* — James O Hansen
*Assistant Examiner* — Matthew Ing
(74) *Attorney, Agent, or Firm* — Wood, Herron & Evans, LLP

(57) ABSTRACT

The present invention relates to a safety workbench having a working chamber enclosed by a housing and a housing front side, which has a work opening, which is closable by an adjustable front pane, the front pane having at least one additional cleaning position, in which it is situated at least partially below a closed final position, in which the work opening is completely covered, in such a way that a cleaning opening is formed between pane top edge and housing. The front pane is easier and safer to clean than the previously known safety workbenches due to this additionally provided cleaning position.

7 Claims, 1 Drawing Sheet

FOREIGN PATENT DOCUMENTS

| | | | |
|---|---|---|---|
| DE | 297 23 636 | U1 | 1/1999 |
| DE | 29723636 | U1 | 1/1999 |
| DE | 100 17 196 | A1 | 10/2001 |
| DE | 102 17 903 | C1 | 10/2003 |
| DE | 10217903 | C1 | 10/2003 |
| DE | 10 2004 032 454 | A1 | 1/2006 |
| GB | 1256238 | | 12/1971 |
| GB | 2240263 | A | 7/1991 |
| GB | 2323785 | A | 10/1998 |

* cited by examiner

SAFETY WORKBENCH HAVING EASY-TO-CLEAN FRONT PANE

CROSS-REFERENCE TO RELATED APPLICATIONS

This application claims priority of German Patent Application DE 102006060407.5 filed Dec. 20, 2006, the contents of which is incorporated by reference in its entirety.

BACKGROUND OF THE INVENTION

The present invention relates to a safety workbench having a front pane which has at least one additional cleaning position.

Safety workbenches fulfill various functions. They are generally used for protecting the products to be manufactured or processed within the workbench, the operator, and/or the environment.

The basic construction of safety workbenches comprises an inner chamber enclosed by a housing and a work opening on the housing front side, which is closable using an adjustable front pane. The inner chamber is also identified in the meaning of the present invention as a working chamber or working inner chamber. Such safety workbenches are already known in greatly varying embodiments from the prior art, for example, from DE 44 41 784 A1, DE 102 17 903 C1, DE 297 23 636, and DE 100 17 196 A1.

The front pane plays a central role in the various protective functions of the safety workbench. It largely closes the working chamber in the working position to the external surroundings and prevent the escape of particles, is used, inter alia, as a spray guard for the operator, and, vice versa, also prevents the penetration of particles from the external surroundings into the working inner chamber.

The front pane may essentially assume three different positions in a safety workbench, namely the open final position, in which the front pane and thus also the work are maximally open, the work position, in which the front pane partially covers the work opening in the top area, and the closed final position, in which the front pane essentially completely closes the work opening.

Safety workbenches in laboratories, in particular those which are suitable for microbiological work, must meet strict safety requirements. They have additional fans and/or exhaust devices, which exhaust air contaminated by particles or aerosols through directed airflows, for example, and thus additionally protect the operators. Such a safety workbench is described, for example, in DE 10 2004 032 454 A1. To ensure safe operation, the front pane may not remain too far open over a long time in such a safety workbench, because the required airflows may not be maintained in the event of too large an opening cross-section of the work opening and thus product and personal protection are not ensured.

In addition, an operator is to be able to see into the working chamber through the front pane of the safety workbench and observe the procedures inside the working chamber. A visual check of the working chamber is thus possible.

For various reasons, it may be necessary to clean the entire working chamber of a safety workbench and thus particularly also the interior of the front pane. On one hand, the particular required cleanness of the entire working inner chamber may also be produced and ensured in this way, for example, also by disinfection. On the other hand, the view and thus the visual check of the procedures within the working chamber may be obstructed by direct contamination and dirtying of the front pane. Contaminants must accordingly be removed.

In the known safety workbenches, the front pane is mounted in such a way that it may be pushed up and down essentially parallel to the housing front side. It is not possible here to clean the complete interior of the front pane. The area which may just not be reached during cleaning is additionally in the normal viewing area of operators, so that the visual check is obstructed.

Other front panes of the prior art have additional hinges or other folding mechanisms. The front pane may be opened upward and cleaned on its interior here. During this procedure, the work opening of the safety workbench is completely open to the surroundings. The surroundings are subjected to possible contamination. In addition, the operator is subjected to the possibly contaminated working inner chamber, because he must inevitably approach closely thereto during the cleaning procedure. It is especially disadvantageous that he nearly automatically has to stand below the front pane to be cleaned in this case.

The safety functions of the front pane are thus disengaged in this open position. The contaminated front pane itself even represents an additional risk.

The front panes of the prior art have the additional disadvantage that the cleaning may only be performed from below the opening of the pane and thus the operator is subject to the danger of being contaminated himself by falling dirt or dripping cleaning liquid. This is an especially grave safety risk if an overhead working position results for the operator during cleaning.

The object of the present invention is therefore to provide a safety workbench having a front pane which overcomes the disadvantages of the prior art and in which the front pane is easier to clean completely, without having to completely expose the working chamber.

This object is achieved by the safety workbench having a working chamber enclosed by a housing and a housing front side, which has a work opening, which is closable by an adjustable front pane, wherein the front pane has at least one additional cleaning position, in which it is situated at least partially below a closed final position, in which the work opening is completely covered, in such a way that a cleaning opening is formed between pane top edge and housing.

SUMMARY OF THE INVENTION

The present invention relates to a safety workbench having a working chamber enclosed by a housing and a housing front side, which has a work opening, which is closable by an adjustable front pane, according to the present invention, the front pane having at least one additional cleaning position, in which it is situated at least partially below a closed final position, in which the work opening is completely covered, in such a way that a cleaning opening is formed between pane top edge and housing. In this special cleaning position of the front pane, an engagement opening thus results as a gap between the top edge of the front pane and the housing section located above it, which delimits the work opening on top. This opening is identified in the meaning of the present invention as a cleaning opening. An operator may reach behind the front pane from above through this cleaning opening and perform cleaning work, so that the pane may thus be cleaned both from above and also from below (when the front pane is placed in the working position)—and thus completely.

It is especially advantageous that no contamination by falling dirt particles or dripping cleaning liquid may result during the cleaning procedure in the safety workbench according to the present invention. In addition, no overhead working situation for the operator may arise.

A further advantage is that the working chamber must only be opened to the extent required for reaching in by the operator. Otherwise, the work opening remains covered by the front pane, so that its protective functions may also essentially be maintained during the cleaning procedure. In particular, the required airflows in the working chamber may also advantageously be maintained. It is thus possible according to the present invention to secure the personal, environmental, and product protection even during the cleaning procedure and meet corresponding safety requirements.

To ensure that the front pane is not lowered too far and thus, for example, too large an opening arises, which no longer allows maintaining the claimed protective parameters, means may expediently be provided which prevent too strong lowering of the front pane. These may be mechanical or other blocks, which prevent lowering beyond a specific final position. For this purpose, it may be advisable to provide a measurement device known per se, using which the pane position may be determined. The pane may be moved into the particular desired position manually or automatically in a typical way via an operating unit integrated in the safety workbench. The operating unit may be programmed in such a way that movement downward beyond the cleaning position is not possible. The cleaning position is expediently selected in such a way that the exposed cleaning opening is not larger than the permissible opening size of the work opening in a working position in which work is performed in the working inner chamber of the safety workbench by an operator. In this case, it is ensured that the prescribed safety conditions are still maintained.

Except for the designs which allow the front pane to be lowered into the cleaning position, the safety workbench according to the present invention may be designed analogously to the safety workbenches known up to this point. The drive devices for the front pane may be fundamentally implemented as in the prior art and only have to be slightly modified to allow lowering beyond the position in which the work opening is completely closed. Guide rails may be provided along the lateral pane edges on both sides in a typical way for the movable mounting of the front pane, for example, in which the pane runs up and down. These guide rails may be open on the bottom on one hand, so that the front pane partially travels downward out of them to reach the cleaning position. This has the advantage that the guide rails do not have to be lengthened in relation to typical safety workbenches. Alternatively, the guide rails may be lengthened, so that the front pane is additionally guided in them over at least some distance upon travel into the cleaning position. If the guide rails are so long that the bottom pane side edges are still mounted in them in the cleaning position, the guide rails may be closed on their bottom end, the closed ends being able to be used as a stopper for the pane.

In a further design of the present invention, the front pane may be implemented in two parts or multiple parts. The use of the front pane may be designed more flexibly in this way and may be tailored to the particular work situation. The parts of the front pane may expediently be adjusted independently from one another in this design. For example, the front pane may be partitioned into a top part and a bottom part. These parts may also be situated partially or completely overlapping. In this embodiment according to the present invention, only the top part of the front pane may advantageously also be lowered into cleaning position. For this purpose, the top part of the front pane is displaced into a position below its closed final position, while the bottom part of the front pane remains in its position of the closed final position. The top part is expediently moved behind the bottom part of the front pane. In this way, the weight of the parts to be moved may be reduced.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The present invention is explained in the following for exemplary purposes on the basis of two embodiment variants in connection with the drawing. The present invention is not restricted to these embodiments.

DETAILED DESCRIPTION

Figure 1:
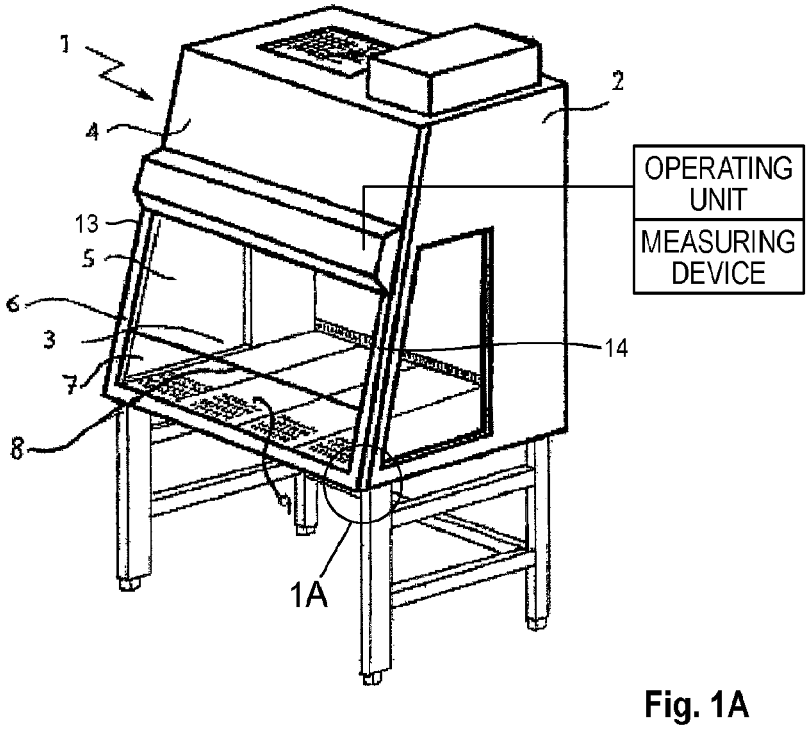
FIG. 1 shows a safety workbench according to the present invention in a perspective illustration in a working position.
Figure 1A:
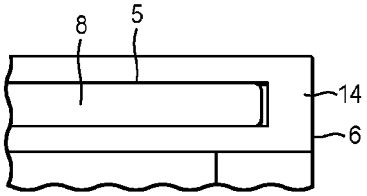
FIG. 1A is an enlargement of the encircled area 1A in FIG. 1 and shows diagrammatically one of the guide rails open on the bottom.

FIG. 1 shows a safety workbench 1 according to the present invention, which may be used in microbiological work, for example. The safety workbench 1 has a housing 2, which encloses a working inner chamber 3. An adjustable front pane 5 is situated on the housing front side 4. The front pane 5 is mounted in a frame 6 in such a way that it may be pushed up and down in lateral guide rails 13, 14 essentially parallel to the housing front side 4. By pushing down the front pane 5, the work opening 7 located on the housing front side 4 may be made smaller. The height of the exposed work opening thus results from the gap between the bottom edge 8 of the front pane 5 and the working chamber floor plate or work level 9. In its closed final position, the bottom edge 8 of the front pane 5 is situated at the same height as the work level 9 and closes the work opening 7 completely. In addition, the safety workbench 1 has the typical components known from the prior art, such as fan, filter, measurement, analysis, control, and regulation devices, an operating unit, etc.

Figure 2:
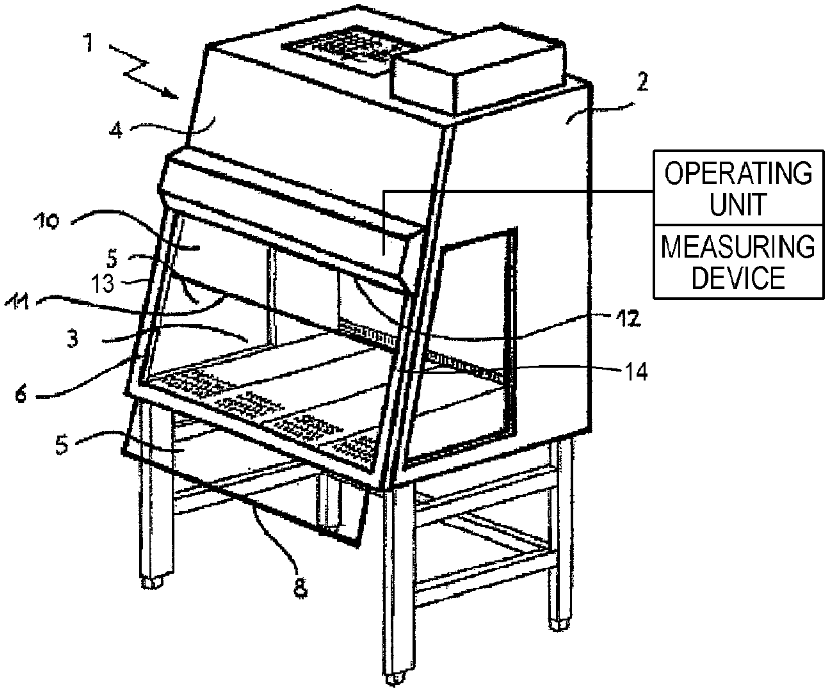
FIG. 2 shows a safety workbench according to the present invention in a perspective illustration having the front pane in a cleaning position.

FIG. 2 shows the safety workbench from FIG. 1, in which the front pane 5 corresponding to the design according to the present invention has been lowered beyond the closed final position into a cleaning position. A cleaning opening 10 thus arises on the top side of the front pane 5, which may be enlarged by pushing down further. The height of the cleaning opening 10 thus results from the gap between the top edge 11 of the front pane 5 and the housing section located above the work opening 7. The front pane 5 projects on the bottom out of its frame 6 and the guide rails 13, 14 in this position.

The front pane 5 typically comprises glass, such as a suitable composite glass. However, it may also be manufactured from another suitable material, for example, from plastic. Instead of the mounting in a frame having guide rails, the front pane 5 may alternatively or additionally be retained by other known retention devices, which allow lowering into a cleaning position according to the present invention.

The ventilation devices, such as fan, circulating air, exhaust air, and filtering devices, correspond to those required according to the particular standards and requirements for safe operation of a safety workbench, and possibly also legally prescribed. Such devices are described, for example, in DE 10 2004 032 454 A1.

The security workbench 1 may additionally have an integrated operating unit for controlling various device functions. This has the advantage that the operation of the safety workbench is not only more comfortable for the operator, but rather the various functions, such as the setting of fan and exhaust devices and the pane position, may also be checked better and the operation is thus safer.

The front pane 5 may be adjusted manually or moved via the operating unit for controlling device functions into the various positions, i.e., also into the cleaning position. The front pane 5 may be fixed in a typical way in any position from the top open final position down to the cleaning position using known locks.

In an advantageous refinement of the present invention, moving the front pane 5 into the cleaning position is only possible in a specially set cleaning mode. This may be set via a special switch in an operating unit, for example. This has the advantage that in normal working operation or working mode of the safety workbench, when the front pane is moved downward, the closed final position may not be passed unintentionally, i.e., it is only possible to intentionally approach the cleaning position. Increased operational reliability is achieved in this way.

The safety workbench 1 according to the present invention may advantageously also have at least one additional safety monitoring device, such as sensors for checking the exhaust or circulating air flow or the air entrance velocity, or a measurement device for measuring the position of the front pane. In this way, the safety workbench may be prevented from being operated in a lowed state unnoticed. These monitoring functions preferably also continue to run during the cleaning phases of the front pane.

Set point values for the various functions may expediently additionally be established using the safety monitoring device, a visual or acoustic alarm being given if the functions exceed or fall below them. Such an alarm function may advantageously also be provided for the case in which a breakdown or defect of a component of the safety workbench is established by the monitoring device. The safety workbench according to the present invention may achieve and ensure increased operational reliability in this way.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

LIST OF REFERENCE NUMERALS

1 safety workbench
2 housing
3 working inner chamber
4 housing front side
5 front pane
6 frame
7 work opening
8 bottom edge of the front pane
9 work level
10 cleaning opening
11 top edge of the front pane
12 upper boundary of the work opening
13 lateral guide rail
14 lateral guide rail

What is claimed is:

1. A safety workbench, comprising:
- a housing having a housing front side and defining an enclosed working space having a floor plate;
- a work opening defined on the housing front side; and
- an adjustable single-piece front pane defined by an upper edge, a lower edge and a pair of opposite side edges supported by the housing and being movable along a linear path between a work position wherein the upper edge of the single-piece front pane is situated above the work opening and the lower edge is located at a height above the floor plate with the single-piece front pane at least partially closing the work opening and a closed position wherein the single-piece front pane completely closes the work opening,
- and further wherein the single-piece front pane is movable along the linear path to a cleaning position wherein the lower edge of the single-piece front pane is situated below the work opening and is located at a height below the floor plate so that a cleaning opening is formed between the upper edge of the single-piece front pane and the housing, such that the safety workbench, when operated with the front pane in the work position, protects products therein and users outside from contamination.

2. The safety workbench according to claim 1, wherein the front pane may be moved manually or automatically via an integrated operating unit into the cleaning position.

3. The safety workbench according to claim 1, further comprising a measuring device configured to measure the position of the front pane.

4. The safety workbench according to claim 1, wherein the front pane may be lowered only to the extent that the size of the cleaning opening is not greater than a permissible size of the work opening in the work position of the safety workbench.

5. The safety workbench according to claim 1, wherein the front pane is mounted in guide rails on its lateral edges.

6. The safety workbench according to claim 5, wherein the guide rails are open on the bottom.

7. The safety workbench according to claim 5, wherein the guide rails extend far enough downward so as to laterally delimit the front pane even in the cleaning position.

* * * * *